United States Patent
Hirai

(10) Patent No.: US 10,064,676 B2
(45) Date of Patent: Sep. 4, 2018

(54) MEDICAL APPARATUS

(71) Applicant: OLYMPUS CORPORATION, Hachioji-shi, Tokyo (JP)

(72) Inventor: Yuji Hirai, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/615,370

(22) Filed: Jun. 6, 2017

(65) Prior Publication Data

US 2017/0265930 A1    Sep. 21, 2017

Related U.S. Application Data

(63) Continuation of application No. PCT/JP2016/062019, filed on Apr. 14, 2016.

(30) Foreign Application Priority Data

Apr. 24, 2015  (JP) ................. 2015-089674

(51) Int. Cl.
*A61B 18/12* (2006.01)
*A61B 18/14* (2006.01)
(Continued)

(52) U.S. Cl.
CPC ............. *A61B 18/14* (2013.01); *A61B 90/57* (2016.02); *A61N 1/0472* (2013.01); *A61B 90/02* (2016.02);
(Continued)

(58) Field of Classification Search
CPC .......... A61B 18/14; A61B 2017/00026; A61B 2017/00106; A61B 90/02; A61B 90/14;
(Continued)

(56) References Cited

U.S. PATENT DOCUMENTS

2007/0198005 A1* 8/2007 Ichihashi ....... A61B 17/320092
606/27
2009/0088667 A1    4/2009 Masuda
(Continued)

FOREIGN PATENT DOCUMENTS

EP    2 105 100 A1    9/2009
JP    2003-79633 A    3/2003
(Continued)

OTHER PUBLICATIONS

Jul. 5, 2016 Search Report issued in International Patent Application No. PCT/JP2016/062019.
(Continued)

*Primary Examiner* — Daniel Fowler
(74) *Attorney, Agent, or Firm* — Oliff PLC

(57) ABSTRACT

A medical apparatus includes a first clamp portion; a pivot shaft; a second clamp portion rotatable around the pivot shaft, and movable between an opened position in which the second clamp portion is distant from the first clamp portion, and a closed position in which the second clamp portion is adjacent to the first clamp portion; and an electrode member provided on the second clamp portion, and opposed to the first clamp portion, the electrode member forming a clearance in cooperation with the first clamp portion in the closed position, the clearance in a second position distant from the pivot shaft being smaller than the clearance in a first position adjacent to the pivot shaft, to adjust holding pressure.

10 Claims, 16 Drawing Sheets

(51) Int. Cl.
*A61B 90/57* (2016.01)
*A61N 1/04* (2006.01)
*A61N 1/18* (2006.01)
*A61B 90/00* (2016.01)
*A61B 17/00* (2006.01)
*A61B 90/14* (2016.01)

(52) U.S. Cl.
CPC ..... *A61B 90/14* (2016.02); *A61B 2017/00026* (2013.01); *A61B 2017/00106* (2013.01); *A61N 1/18* (2013.01)

(58) Field of Classification Search
CPC . A61B 90/57; A61B 18/1442; A61B 18/1445; A61B 18/1447; A61B 2018/145; A61B 2018/1452; A61B 2018/1455; A61B 2018/1457; A61B 2018/146; A61N 1/0472; A61N 1/18
See application file for complete search history.

(56) References Cited

U.S. PATENT DOCUMENTS

2009/0248051 A1* 10/2009 Masuda ......... A61B 17/320092
606/169
2011/0184404 A1 7/2011 Walberg et al.

FOREIGN PATENT DOCUMENTS

| | | |
|---|---|---|
| JP | 2009-082710 A | 4/2009 |
| JP | 2009-207666 A | 9/2009 |
| JP | 2009-240773 A | 10/2009 |
| WO | 2005/120376 A2 | 12/2005 |
| WO | 2014/148281 A1 | 9/2014 |

OTHER PUBLICATIONS

Jul. 5, 2016 Translation of Written Opinion issued in International Application No. PCT/JP2016/062019.
Jun. 28, 2018 Extended European Search Report issued in European Patent Application No. 16783088.4.

* cited by examiner

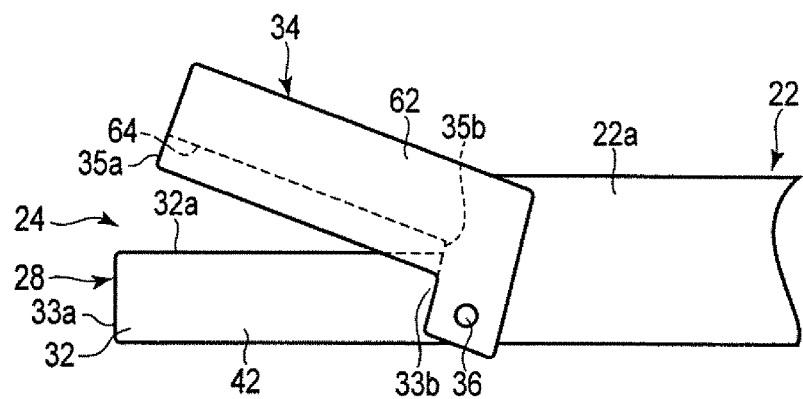
F I G. 3A
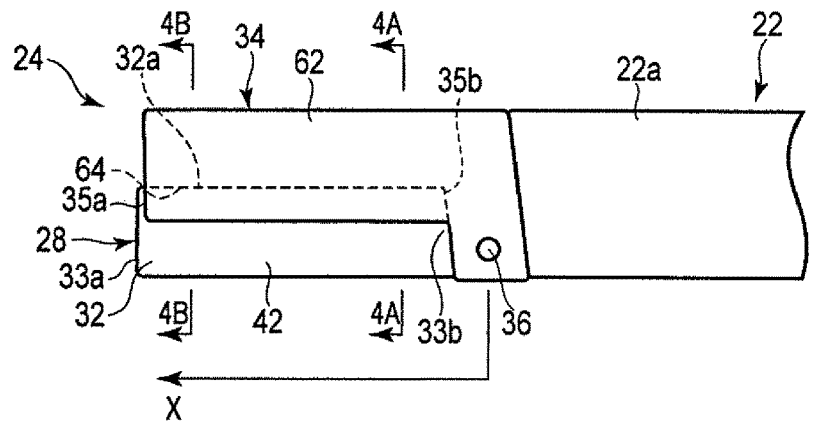
F I G. 3B
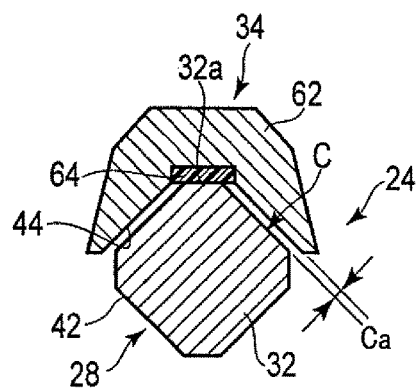
F I G. 4A

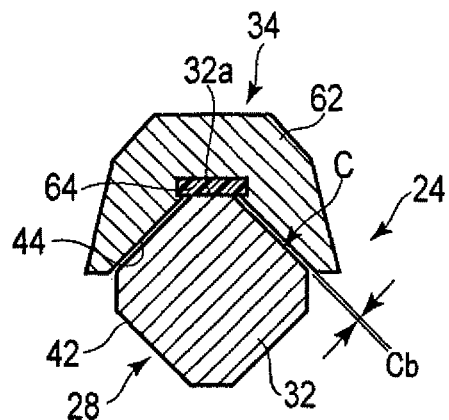
F I G. 4B
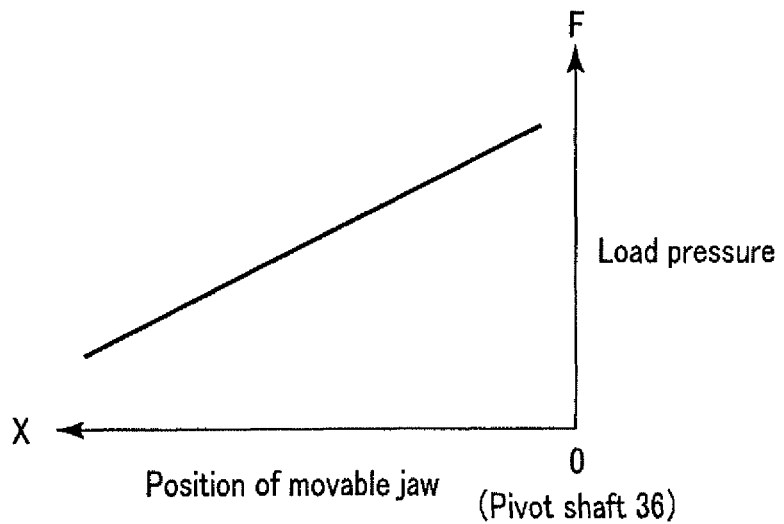
F I G. 5A

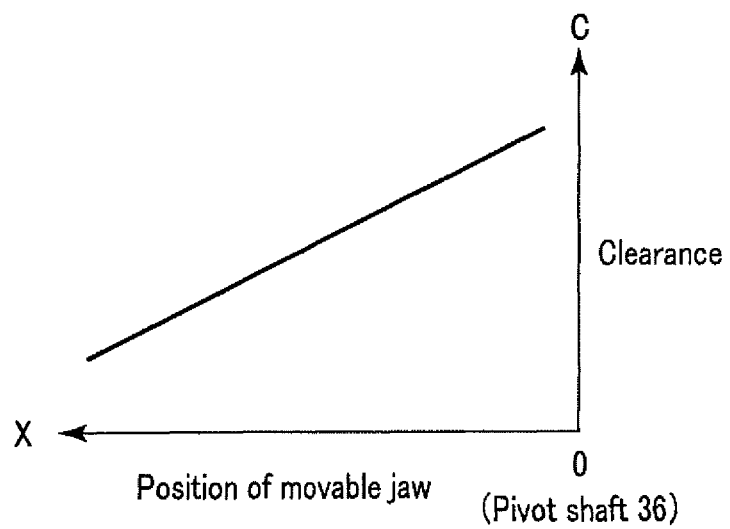
F I G. 5B
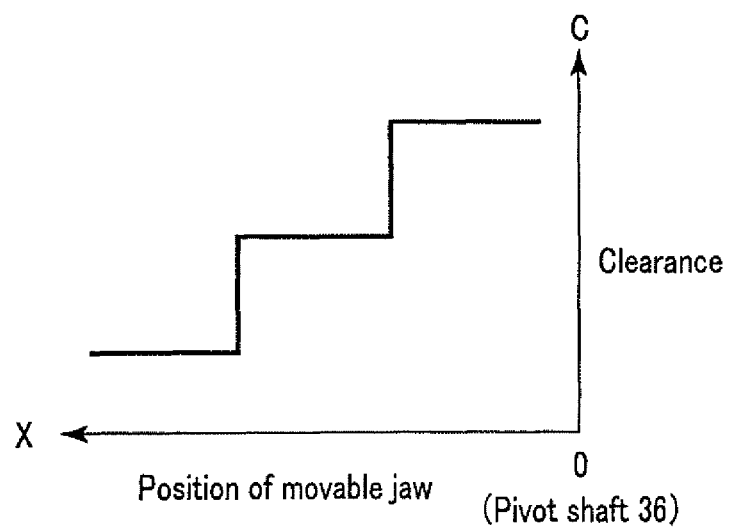
F I G. 5C

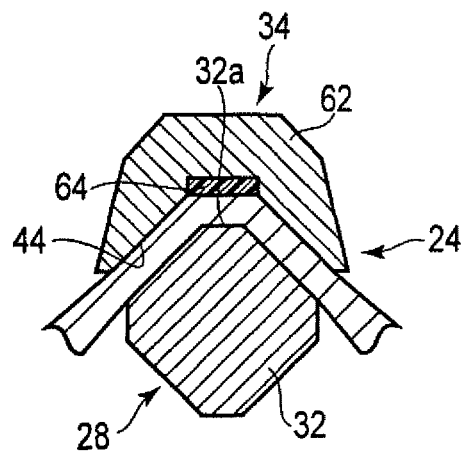
F I G. 6A
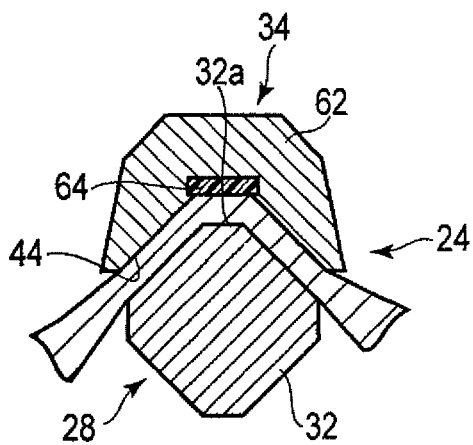
F I G. 6B

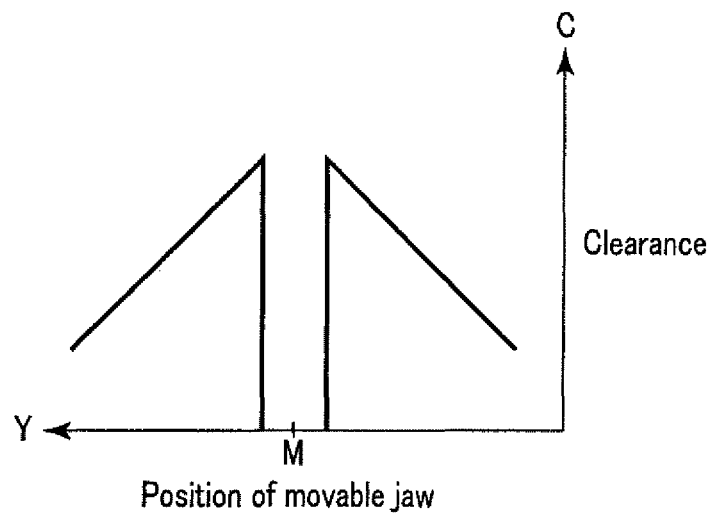
F I G. 9B
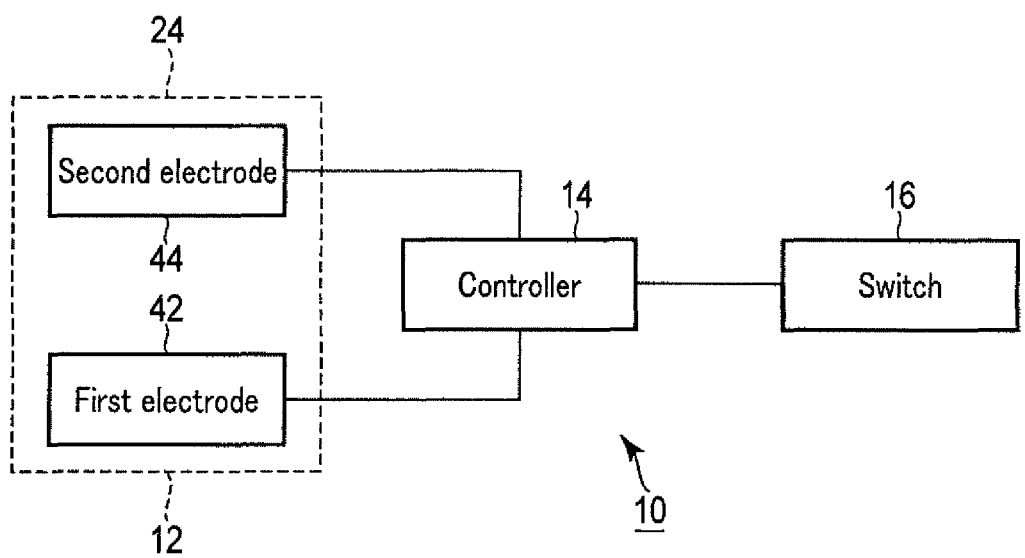
F I G. 10

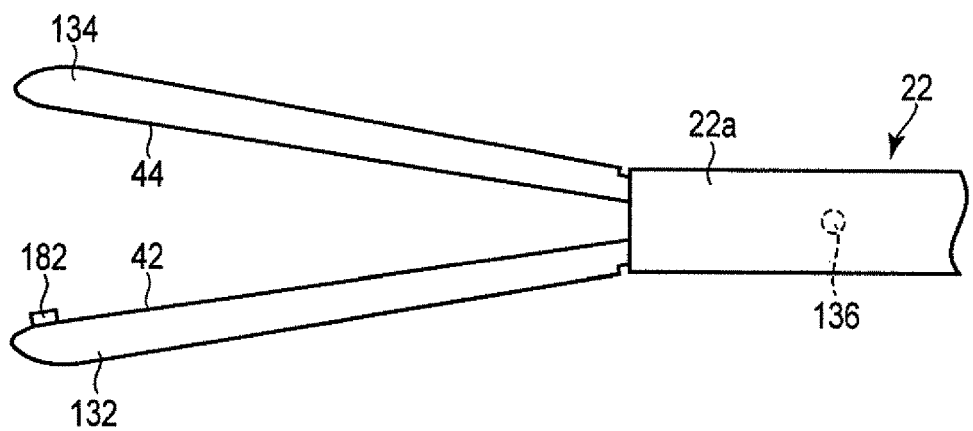
F I G. 11A
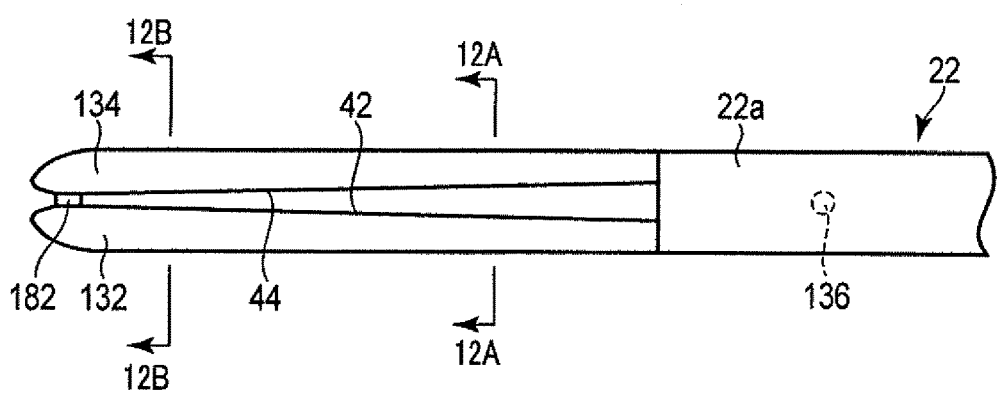
F I G. 11B
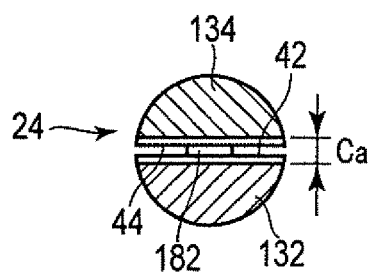
F I G. 12A

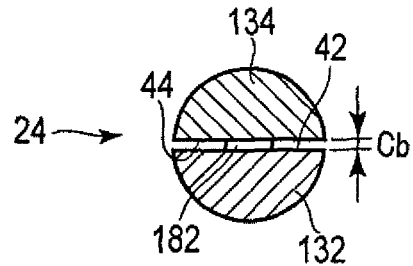
F I G. 12B
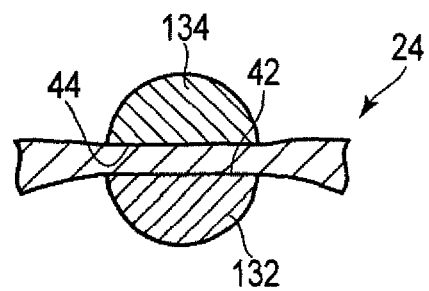
F I G. 13A
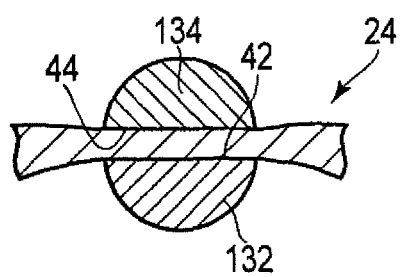
F I G. 13B

MEDICAL APPARATUS

CROSS-REFERENCE TO RELATED APPLICATIONS

This application is a Continuation application of PCT Application No. PCT/JP2016/062019, filed Apr. 14, 2016 and based upon and claiming the benefit of priority from prior Japanese Patent Application No. 2015-089674, filed Apr. 24, 2015, the entire contents of all of which are incorporated herein by reference.

BACKGROUND OF THE INVENTION

1. Field of the Invention

The present invention relates to a medical apparatus holding a living tissue to perform treatment.

2. Description of the Related Art

For example, as disclosed in US 2009/088667 A1, a medical apparatus is disclosed with a structure in which a second clamp portion movable with respect to a first clamp portion is rotated with a pivot shaft serving as a fulcrum, to apply a load pressure to a living tissue of various types and hold the living tissue.

BRIEF SUMMARY OF THE INVENTION

According to one aspect of the present invention, a medical apparatus includes a first clamp portion; a pivot shaft; a second clamp portion rotatable around the pivot shaft, and movable between an opened position in which the second clamp portion is distant from the first clamp portion, and a closed position in which the second clamp portion is adjacent to the first clamp portion; and an electrode member provided on the second clamp portion, and opposed to the first clamp portion, the electrode member forming a clearance in cooperation with the first clamp portion in the closed position, the clearance in a second position distant from the pivot shaft being smaller than the clearance in a first position adjacent to the pivot shaft, to adjust holding pressure.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 3A is a schematic diagram illustrating a state of an opened position in which a movable jaw (clamp portion) is opened with respect to a stationary jaw (clamp portion) of the treatment instrument of the medical apparatus unit according to the first embodiment;

FIG. 3B is a schematic diagram illustrating a state of a closed position in which the movable jaw is closed with respect to the stationary jaw of the treatment instrument of the medical apparatus unit according to the first embodiment;

FIG. 4A is a schematic lateral cross-sectional view in a position along line 4A-4A in FIG. 3B;

FIG. 4B is a schematic lateral cross-sectional view in a position along line 4B-4B in FIG. 3B;

FIG. 5A is a schematic diagram illustrating load pressure with respect to the position of the movable jaw at the time when the load pressure is to be applied to the living tissue, in a state where the movable jaw is rotated to the closed position with the pivot shaft of the treatment instrument according to the first embodiment serving as the fulcrum;

FIG. 5B is a schematic diagram illustrating a size of clearance from the stationary jaw with respect to the position of the movable jaw, in the state where the movable jaw is rotated to the closed position with the pivot shaft of the treatment instrument according to the first embodiment serving as the fulcrum;

FIG. 5C is a schematic diagram illustrating a size of clearance from the stationary jaw with respect to the position of the movable jaw, in the state where the movable jaw is rotated to the closed position with the pivot shaft of the treatment instrument according to a modification of the first embodiment serving as the fulcrum;

FIG. 6A is a schematic lateral cross-sectional view illustrating a state where the living tissue is held in the position along line 4A-4A in FIG. 3B;

FIG. 6B is a schematic lateral cross-sectional view illustrating a state where the living tissue is held in the position along line 4B-4B in FIG. 3B;

FIG. 9B is a schematic diagram illustrating a size of clearance from the stationary jaw with respect to the position of the movable jaw, in the state where the movable jaw is rotated to the closed position with the pivot shaft of the treatment instrument according to the first modification of the first embodiment serving as the fulcrum;

FIG. 10 is a schematic block diagram illustrating a medical apparatus unit according to a second embodiment;

FIG. 11A is a schematic diagram illustrating a state of an opened position in which first and second jaws (clamp portions) of a treatment instrument of the medical apparatus unit according to the second embodiment are opened;

FIG. 11B is a schematic diagram illustrating a state of an closed position in which the first and second jaws of the treatment instrument of the medical apparatus unit according to the second embodiment are closed;

FIG. 12A is a schematic lateral cross-sectional view in a position along line 12A-12A in FIG. 11B;

FIG. 12B is a schematic lateral cross-sectional view in a position along line 12B-12B in FIG. 11B;

FIG. 13A is a schematic lateral cross-sectional view illustrating a state where the living tissue is held in the position along line 12A-12A in FIG. 11B;

FIG. 13B is a schematic lateral cross-sectional view illustrating a state where the living tissue is held in the position along line 12B-12B in FIG. 11B;

DETAILED DESCRIPTION OF THE INVENTION

Embodiments of the present invention will be explained hereinafter with reference to drawings.

[First Embodiment]

A first embodiment will be explained hereinafter with reference to FIG. 1 to FIG. 6B.

Figure 1:
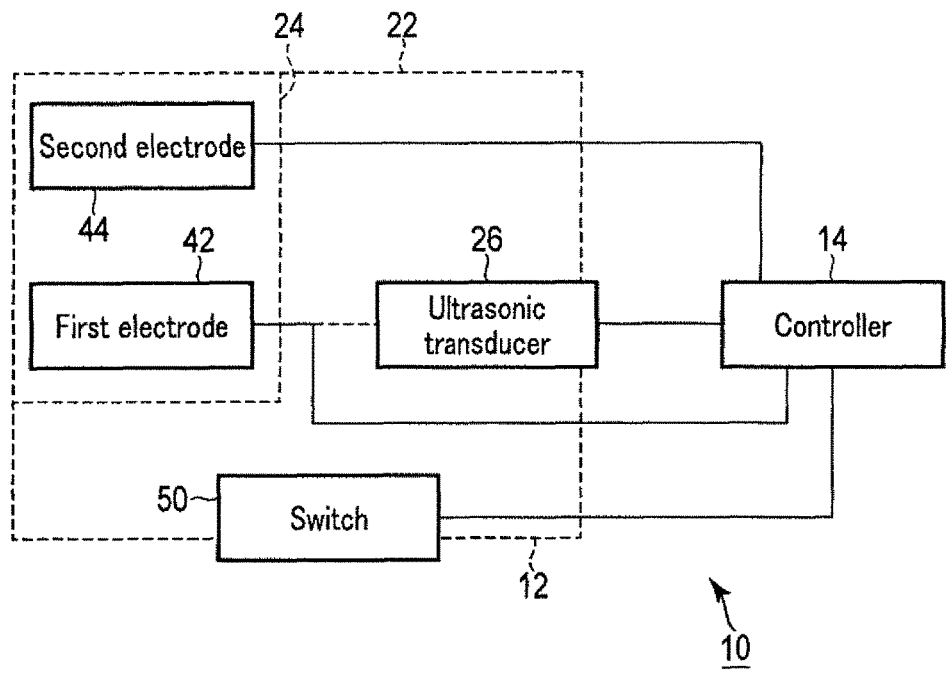
FIG. 1 is a schematic block diagram illustrating a medical apparatus unit according to a first embodiment.

As illustrated in FIG. 1, a treatment unit 10 according to the present embodiment includes a treatment instrument (medical apparatus) 12, and a controller 14 including a power supply. The treatment instrument 12 and the controller 14 are preferably detachable.

Figure 2:
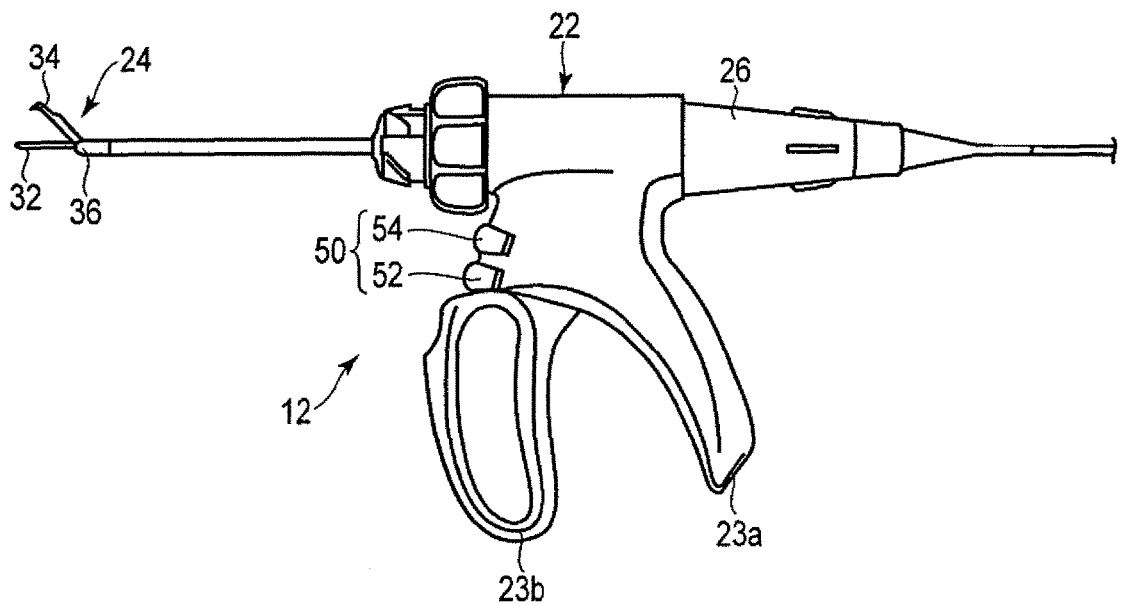
FIG. 2 is a schematic diagram illustrating a treatment instrument (medical apparatus) of the medical apparatus unit according to the first embodiment.

As illustrated in FIG. 2, the treatment instrument 12 includes a treatment instrument main body 22, and a treatment section (end effector) 24. The treatment instrument 12 further includes an ultrasonic transducer 26 that is preferably attachable to and detachable from the treatment instrument main body 22. The ultrasonic transducer 26 is connected with an ultrasonic probe (vibration transmission member) 28 capable of transmitting ultrasonic vibration generated in the ultrasonic transducer 26. The ultrasonic probe 28 is formed of a material having conductivity, such as titanium alloy and the like. The distal end portion (probe distal end portion) of the ultrasonic probe 28 projects from the distal end of the treatment instrument main body 22, and is used as a stationary jaw 32 described later.

As illustrated in FIG. 3A and FIG. 3B, the treatment section 24 includes the stationary jaw (first clamp portion) 32 and a movable jaw (second clamp portion) 34. The movable jaw 34 is movable between an opened position in which the movable jaw 34 is distant from the stationary jaw 32, and a closed position in which the movable jaw 34 is adjacent to the stationary jaw 32.

The movable jaw 34 is supported by the treatment instrument main body 22. More specially, the movable jaw 34 is supported by a pivot shaft 36 at the distal end of a sheath 22a. The movable jaw 34 is rotatable around the pivot shaft 36, and movable between the position (opened position) illustrated in FIG. 3A in which the movable jaw 34 is distant from the stationary jaw 32, and the position (closed position) illustrated in FIG. 3B in which the movable jaw 34 is adjacent to the stationary jaw 32. The treatment section 24 also includes a first electrode (electrode member) 42 formed as the probe distal end portion (first clamp portion) 32 connected with the ultrasonic transducer 26, and a secondelectrode (second electrode member) 44 provided on the movable jaw 34. As illustrated in FIG. 1, the treatment instrument main body 22 includes a switch 50. The first electrode 42, the second electrode 44, the ultrasonic transducer 26 and the switch 50 are electrically connected with the controller 14. The first electrode 42 and the second electrode 44 have different potentials.

As illustrated in FIG. 2, in the present embodiment, the switch 50 includes a first switch 52 and a second switch 54. When the first switch 52 is pressed, a signal is input from the first switch 52 to the controller 14. At the time, the controller 14 controls the first and second electrodes 42 and 44 to perform bipolar high-frequency output in a seal mode. For this reason, when the first switch 52 is pressed, coagulation of the living tissue (seal of the blood vessel when the living tissue is the blood vessel) can be performed. When the second switch 54 is pressed, a signal is input from the second switch 54 to the controller 14. At the time, the controller 14 performs ultrasonic output and bipolar high-frequency output in a seal & cut mode. For this reason, when the second switch 54 is pressed, coagulation and incision of the living tissue (seal and incision of the blood vessel when the living tissue is the blood vessel).

As illustrated in FIG. 2, the treatment instrument main body 22 includes a stationary handle 23a and a movable handle 23b. The treatment section 24 of the treatment instrument 12 according to the present embodiment is formed in a single-swinging type. The movable jaw 34 is opened with respect to the stationary jaw 32, in linkage with an operation of moving the movable handle 23d of the treatment instrument main body 22 to be distant from the stationary handle 23a. The movable jaw 34 is closed with respect to the stationary jaw 32, in linkage with an operation of moving the movable handle 23d of the treatment instrument main body 22 to be adjacent to the stationary handle 23a. Specifically, in the treatment section 24, the movable jaw 34 is openable and closable with respect to the stationary jaw 32. By closing the movable jaw 34 with respect to the stationary jaw 32, the living tissue is held between the stationary jaw 32 and the movable jaw 34. A publicly-known mechanism of various types may be properly used as the mechanism to open and close the movable jaw 34 with respect to the stationary jaw 32, and explanation thereof is omitted herein.

As illustrated in FIG. 4A and FIG. 4B, the cross section of the stationary jaw (probe distal end portion) 32 is formed in a substantially octagonal shape. The stationary jaw 32 is used as the first electrode 42 to perform high-frequency output to the living tissue in cooperation with the second electrode 44.

The movable jaw 34 includes a movable jaw main body 62 and a pressure pad (stopper) 64. The movable jaw main body 62 is provided with the second electrode 44 in a position opposed to the first electrode 42. The second electrode 44 is formed in a state of holding the pressure pad 64 therebetween. The movable jaw main body 62 is also preferably formed in one unitary piece with the second electrode 44. The pressure pad 64 is formed of a material having electric insulation property, heat resistance, and abrasion resistance. The pressure pad 64 is in a position that can contact a holding surface 32a of the stationary jaw 32. By contrast, the second electrode 44 of the movable jaw 34 can be adjacent to the stationary jaw 32, that is, the first electrode 42, with clearance C.

The stationary jaw 32 and the movable jaw 34 include distal end portions (one end portions) 33a and 35a, and proximal end portions (the other end portions) 33b and 35b, respectively. The proximal end portions (the other end portions) 33b and 35b are adjacent to the pivot shaft 36, and disposed in the vicinity of the most proximal end of the position in which the living tissue can be held. The clearance C is continuously formed from the distal end portions (one end portions) 33a and 35a of the stationary jaw 32 and the movable jaw 34 to the proximal end portions (the other end portions) 33b and 35b. Specifically, in the state where the movable jaw 34 is in the closed position with respect to the stationary jaw 32, the first and second electrodes 42 and 44 are distant from each other from the distal end portions (one end portions) 33a and 35a of the stationary jaw 32 and the movable jaw 34 to the proximal end portions (the other end portions) 33b and 35b. In the stationary jaw 32, a portion between the distal end portion (one end portion) 33a and the proximal end portion (the other end portion) 33b may be straight or curved. In the movable jaw 34, a portion between the distal end portion (one end portion) 35a and the proximal end portion (the other end portion) 35b may be straight or curved. In this example, to simplify the explanation, the explanation illustrates the case where the stationary jaw 32 and the movable jaw 34 are straight.

When the movable handle 23b is moved to be relatively adjacent to the stationary handle 23a of the treatment instrument main body 22, the movable jaw 34 is rotated around the pivot shaft 36 at the distal end of the treatment instrument main body 22 in linkage with the operation of the movable handle 23b, and the movable jaw 34 is moved adjacent to the stationary jaw 32. When the movable handle 23b is moved to be relatively distant from the stationary handle 23a, the movable jaw 34 is rotated around the pivot shaft 36 in linkage with the operation of the movable handle 23b, and the movable jaw 34 is moved distant from the stationary jaw 32.

The stationary jaw 32 and the movable jaw 34 are formed to have a larger size in the longitudinal direction than that in the width direction. The maximum widths of the stationary jaw 32 and the movable jaw 34 are determined based on, for example, the internal diameter of the trocar.

As illustrated in FIG. 3B, the X-axis is determined with the pivot shaft 36 as the origin O. In particular, the X-axis is determined toward the extending direction opposite to the treatment instrument main body 22, from the pivot shaft 36 of the movable jaw 34.

In the state of the closed position in which the movable jaw 34 is adjacent to the stationary jaw 32, pressure (load pressure) F applicable to the living tissue by the pressure pad 64 of the movable jaw 34 along its longitudinal direction (X-axis direction) is schematically distributed in a state illustrated in FIG. 5A. The load pressure F applicable to the living tissue held between the movable jaw 34 and the stationary jaw 32, that is, the load pressure F in the closed position decreases as the distance from the pivot axis 36 increases. This is considered to be caused by deflection of the movable jaw 34 and the stationary jaw 32. For this reason, in the state where the movable jaw 34 is closed with respect to the stationary jaw 32, the movable jaw 34 is capable of applying a large pressure as the position becomes adjacent to the pivot shaft 36, and a small pressure as the position becomes distant from the pivot shaft 36, to the living tissue held between the movable jaw 34 and the stationary jaw 32, as illustrated in FIG. 5A.

The treatment section 24 illustrated in FIG. 3B holds no living tissue. In this state, in the state where the movable jaw 34 is closed with respect to the stationary jaw 32, the gap (clearance) Ca between the second electrode 44 of the movable jaw 34 illustrated in FIG. 4A and the stationary jaw 32 serving as the first electrode 42 is larger than the gap (clearance) Cb illustrated in FIG. 4B. As illustrated in FIG. 5B, the clearance C between the second electrode 44 of the movable jaw 34 and the stationary jaw 32 serving as the first electrode 42 according to the present embodiment increases as the position becomes adjacent to the pivot shaft 36, and decreases as the position becomes distant from the pivot shaft 36 along the X-axis. Specifically, the clearance C between the second electrode 44 of the movable jaw 34 and the stationary jaw 32 serving as the first electrode 42 is formed to satisfy "Ca>Cb".

As illustrated in FIG. 5B, the clearance C is linearly (in a straight line manner) reduced from the position adjacent to the pivot shaft 36 toward the position distant from the pivot shaft 36 along the X-axis. For example, the clearance Ca is, for example, substantially 0.2 mm in the position illustrated in FIG. 4A, and the clearance Cb is, for example, substantially 0.1 mm in the position illustrated in FIG. 4B. The clearance C (>0) larger than 0 is maintained along the X-axis, between the second electrode 44 of the movable jaw 34 and the stationary jaw 32 serving as the first electrode 42.

The clearance C may be formed by adjusting the width in the width direction orthogonal to the X-axis in each position in the direction along the X-axis in the stationary jaw 32 serving as the first electrode 42, or adjusting the shape of the second electrode 44 of the movable jaw 34 orthogonal to the X-axis in each position in the direction along the X-axis.

The following is explanation of operations of the treatment instrument 12 according to the present embodiment.

The operator properly holds the treatment instrument 12, and properly operates the movable handle 23b with respect to the stationary handle 23a, to hold the living tissue (such as a blood vessel) between the stationary jaw 32 and the movable jaw 34.

In this state, the load pressure by the movable jaw 34 of the treatment section 24 substantially linearly decreases as the position becomes distant from the position adjacent to the pivot shaft 36 along the X-axis, as illustrated in FIG. 5A. As illustrated in FIG. 4A, FIG. 4B, and FIG. 5B, the clearance C between the first electrode 42 of the stationary jaw 32 and the second electrode 44 of the movable jaw 34 increases as the position becomes adjacent to the pivot shaft 36, and decreases as the position becomes distant from the position adjacent to the pivot shaft 36 along the X-axis. More specifically, as illustrated in FIG. 5B, the clearance C between the stationary jaw 32 and the movable jaw 34 is formed to be narrowed from the pivot shaft 36 toward the distal end along the X-axis. For this reason, the load pressure F of the movable jaw 34 decreases as the position becomes distant from the pivot shaft 36 along the X-axis. However, the clearance C between the first electrode 42 of the stationary jaw 32 and the second electrode 44 of the movable jaw 34 is reduced, to compensate the load pressure F to crush the living tissue. For this reason, the clearance C in the second position distant from the pivot shaft 36 is formed smaller than that in the first position adjacent to the pivot shaft 36, to adjust the holding pressure of the stationary jaw 32 and the movable jaw 34.

The treatment section 24 holds, for example, a blood vessel having a longitudinal direction in a direction orthogonal to the X-axis. In this state, the blood vessel illustrated in FIG. 6A illustrating the cross section (cross section in the first position) along line 4A-4A in FIG. 3B and the blood vessel illustrated in FIG. 6B illustrating the cross section (cross section in the second position) along line 4B-4B in FIG. 3B is crushed in the same manner. In this state, the crush amounts of the blood vessel illustrated in FIG. 6A and FIG. 6B are substantially the same, and the clearance C is substantially the same in the positions illustrated in FIG. 6A and FIG. 6B.

When the operator presses, for example, the first switch 52, the blood vessel is sealed with high-frequency output. When the blood vessel is sealed with high-frequency output, the blood vessel is held with a substantially uniform thickness as illustrated in FIG. 6A and FIG. 6B. For this reason, the blood vessel is substantially uniformly sealed from the side adjacent to the pivot shaft 36 to the side distant from the pivot shaft 36.

By contrast, when the operator presses, for example, the second switch 54, the blood vessel is cut with ultrasonic output, while being sealed with high-frequency output. When the high-frequency output and the ultrasonic output are simultaneously output to cut the blood vessel while sealing the blood vessel, the blood vessel is substantially uniformly sealed as described above. For this reason, the blood vessel is cut in a state where miss of seal hardly occurs.

As described above, the following can be said with the treatment instrument 12 according to the present embodiment.

The load pressure F of the movable jaw 34 decreases along the longitudinal direction (X-axis) in the direction distant from the pivot shaft 36. The crushing pressure of the living tissue can be compensated by adjusting, gradually reducing in this example, the clearance C between the first electrode 42 of the stationary jaw 32 and the second electrode 44 of the movable jaw 34. This structure substantially equalizes the crush amount between the crush amount with which the living tissue is crushed in the position adjacent to the pivot shaft 36 and the crush amount with which the living tissue is crushed in the position distant from the pivot shaft 36 along the X-axis. Specifically, even when the load pressure F applied to the living tissue held between the stationary jaw 32 and the movable jaw 34 differs along the X-axis, the living tissue can be held with substantially uniform force through the whole length of the region of the held living tissue, by adjusting the clearance C. This structure enables exertion of substantially uniform force, regardless of the position along the X-axis, in the stationary jaw 32 and the movable jaw 34. This structure enables uniform input of energy between the side adjacent to the pivot shaft 36 and the side distant from the pivot shaft 36, when the high-frequency energy is output to the living tissue. This structure substantially equalizes the sealing capability of the living tissue such as a blood vessel, from the side adjacent to the pivot shaft 36 to the side distant from the pivot shaft 36 along the X-axis.

In addition, when the living tissue such as a blood vessel is cut, the sealing capability is substantially equalized. This structure more securely prevents occurrence of miss of seal of the blood vessel when the blood vessel is cut, and leakage of the blood.

Also when the living tissue is coagulated using high-frequency output, the living tissue can be substantially uniformly coagulated in the same manner as the blood vessel. In addition, the sealing capability is substantially equalized when the living tissue is cut. This structure more securely prevents occurrence of miss of coagulation of the living tissue when the living tissue is cut.

The present embodiment illustrates the example of forming the clearance C as illustrated in FIG. 5B. As another example, as illustrated in FIG. 5C, the clearance C may preferably be reduced in a stepped manner, as the position becomes distant from the pivot shaft 36 along the X-axis.

In this case, the holding force to the living tissue can be adjusted in accordance with the position apart from the pivot shaft 36, that is, the position with respect to the pivot shaft 36. For this reason, the treatment section 24 is capable of changing the holding force to the living tissue in accordance with the position along the longitudinal direction.

The method of reducing the clearance C as the position becomes distant from the pivot shaft 36 is not limited to the state illustrated in FIG. 5B or the state illustrated in FIG. 5C, but may be reduced, for example, in a parabolic manner, or in a quadric curve manner.

Figure 7A:
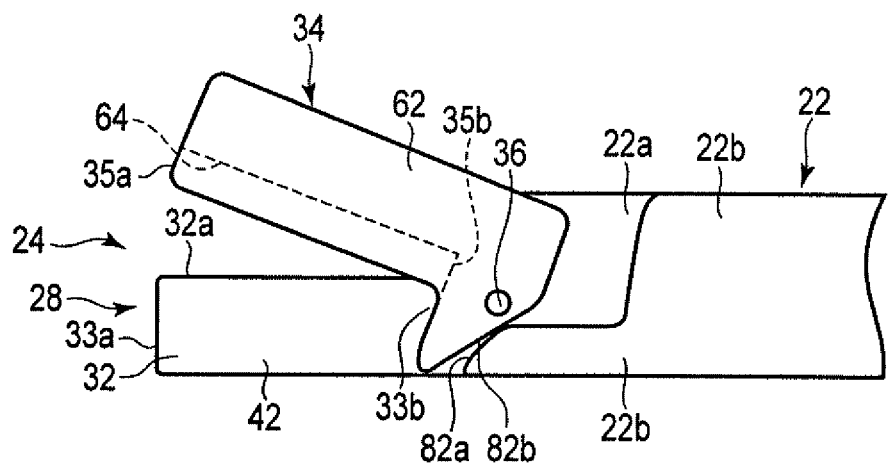
FIG. 7A is a schematic diagram illustrating a state of the opened position in which the movable jaw is opened with respect to the stationary jaw of the treatment instrument of the medical apparatus unit according to a first modification of the first embodiment.
Figure 7B:
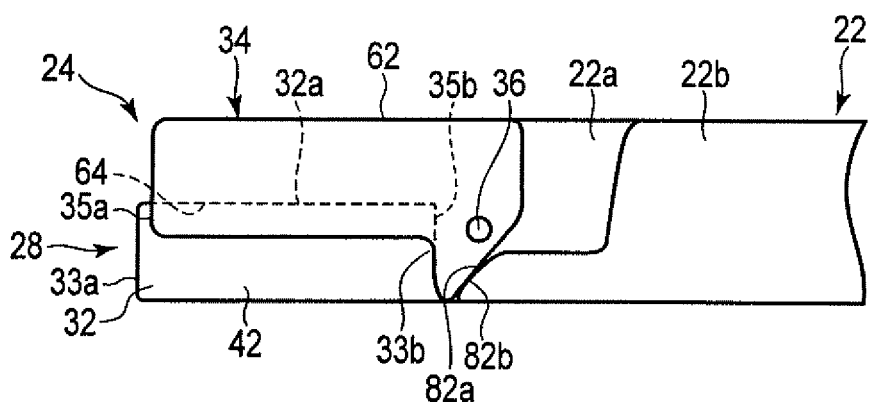
FIG. 7B is a schematic diagram illustrating a state of the closed position in which the movable jaw is closed with respect to the stationary jaw of the treatment instrument of the medical apparatus unit according to the first modification of the first embodiment.

The following is explanation of a first modification of the first embodiment with reference to FIG. 7A and FIG. 7B.

The treatment instrument main body 22 illustrated in FIG. 7A and FIG. 7B includes double sheaths 22a and 22b that are concentrically arranged. In the example, the movable jaw 34 is supported with the pivot shaft 36 at the distal end of the inner sheath 22a of the treatment instrument main body 22. By the movable handle 23b is operated with respect to the stationary handle 23a, the inner sheath 22a and the outer sheath 22b are relatively moved along the axial direction of the sheaths 22a and 22b. For this reason, the stationary jaw 32 and the movable jaw 34 are opened and closed as illustrated in FIG. 7A and FIG. 7B.

The distal end of the outer sheath 22b and the proximal end of the movable jaw 34 are provided with contact sections (stoppers) 82a and 82b, respectively. The contact sections 82a and 82b can be separated from each other as illustrated in FIG. 7A, and can contact each other as illustrated in FIG. 7B. The contact sections (stoppers) 82a and 82b regulate the range in which the movable jaw 34 is rotated around the pivot shaft 36, and regulates the clearance C of the electrode 44 with respect to the electrode 42 of the stationary jaw 32.

For this reason, in the closed state illustrated in FIG. 7B, the clearances Ca and Cb illustrated in FIG. 4A and FIG. 4B can be adjusted by controlling the pivot amount of the movable jaw 34 with respect to the stationary jaw 32.

When the stationary jaw 32 is not used as the ultrasonic probe 28 but used as the high-frequency electrode 42, the clearance C is formed along the opening/closing direction of the movable jaw 34. This structure removes the necessity for providing the electrodes 42 and 44 with electric insulating projections, and enables the electrodes 42 and 44 with larger areas.

Figure 8:
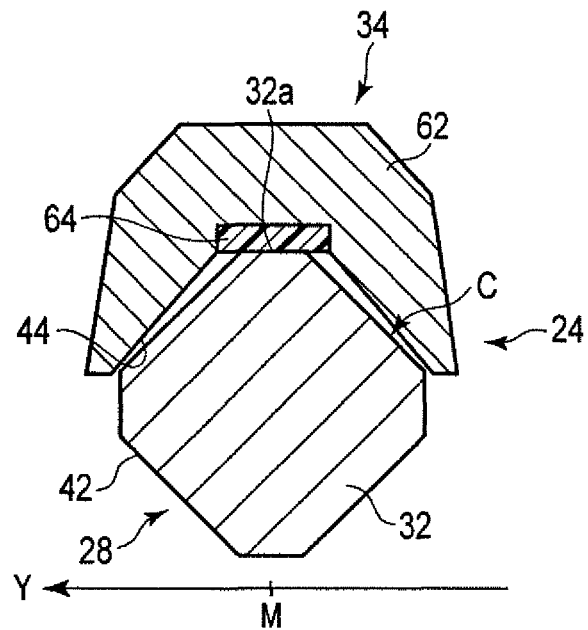
FIG. 8 is a schematic lateral cross-sectional view in the position along line 4A-4A in FIG. 3B.

The following is explanation of a second modification of the first embodiment, with reference to FIG. 8 to FIG. 9B. The clearance C according to the modification is preferably adjusted together with the clearance C explained in the first embodiment.

As illustrated in FIG. 8, a Y-axis is set in a direction orthogonal to a proper position along the X-axis between the pivot shaft 36 and the distal end portions 33a and 35a of the stationary jaw 32 and the movable jaw 32 in FIG. 3B.

Figure 9A:
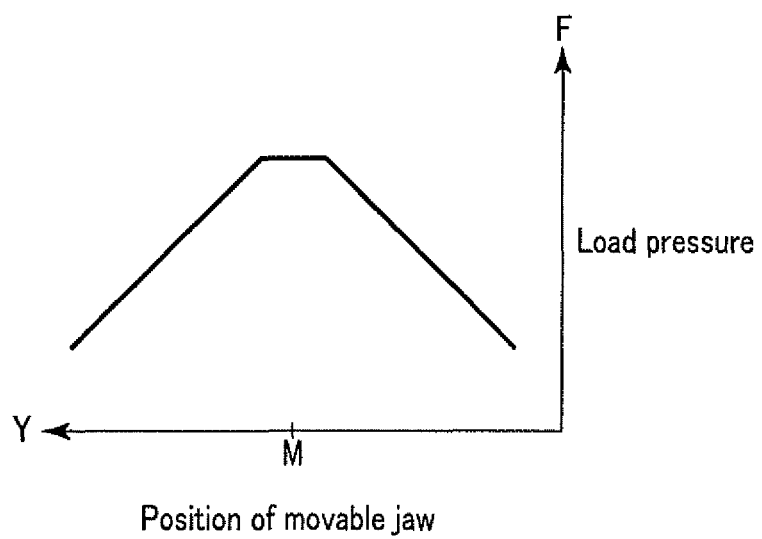
FIG. 9A is a schematic diagram illustrating load pressure with respect to the position of the movable jaw at the time when the load pressure is to be applied to the living tissue, in a state where the movable jaw is rotated to the closed position with the pivot shaft of the treatment instrument according to the first modification of the first embodiment serving as the fulcrum.

In a state of the closed position in which the movable jaw is adjacent to the stationary jaw 32, the pressure (load pressure) F applicable to the living tissue by the pressure pad 64 of the movable jaw 34 along a direction orthogonal to its longitudinal direction schematically distributes in a state illustrated in FIG. 9A. The load pressure F applicable to the living tissue held between the movable jaw 34 and the stationary jaw 32, that is, the load pressure F in the closed position decreases from the substantial center in the width direction of the stationary jaw 32 and the movable jaw 34, as it goes away from the center along the Y direction. This is considered to be caused by deflection of the movable jaw 34 and the stationary jaw 32. For this reason, in the state where the movable jaw 34 is closed with respect to the stationary jaw 32, as illustrated in FIG. 9A, the movable jaw 34 is capable of applying a large pressure gradually increasing toward the substantial center in the width direction of the stationary jaw 32 and the movable jaw 34, and a small pressure gradually decreasing in a direction of going away from the center, to the living tissue held between the movable jaw 34 and the stationary jaw 32. The portion with a fixed applied pressure in the center in FIG. 9A corresponds to a portion in which the holding surface 32a of the stationary jaw 32 (first electrode 42) contacts the pressure pad 64 of the movable jaw 34 in FIG. 8, and the portion includes the middle point M of the movable jaw 34 and the stationary jaw 32.

The treatment section 24 illustrated in FIG. 3B holds no living tissue. In this state, in the state where the movable jaw 34 is closed with respect to the stationary jaw 32, C is the gap (clearance) between the second electrode 44 of the movable jaw 34 and the stationary jaw 32 serving as the first electrode 42 illustrated in FIG. 8. As illustrated in FIG. 9B, the clearance C between the second electrode 44 of the movable jaw 34 and the stationary jaw 32 serving as the first electrode 42 is larger in a position closer to the substantial center in the width direction of the stationary jaw 32 and the movable jaw 34, and smaller in a position more distant from the substantial center in the width direction of the stationary jaw 32 and the movable jaw 34 along the Y-axis, except for the position in which the stationary jaw 32 contacts the pressure pad 64 of the movable jaw 34. In addition, by setting the clearance C between the first electrode 42 of the stationary jaw 32 and the second electrode 44 of the movable jaw 34 is set to be smaller in a position more distant from the substantial center in the width direction of the stationary jaw 32 and the movable jaw 34, the load pressure F to crush the living tissue is compensated. In addition, as explained in the first embodiment, substantially fixed holding force to the living tissue can be exhibited, regardless of the position along the X direction, in the stationary jaw 32 and the movable jaw 34. Accordingly, for example, the blood vessel is substantially uniformly sealed from the substantial center to the distant sides of the stationary jaw 32 and the movable jaw 34. This structure substantially equalizes the sealing capability of the living tissue such as a blood vessel, from the side adjacent to the pivot shaft 36 to the side distant from the pivot shaft along the X-axis, and substantially equalizes the sealing capability from the substantial center in the width direction of the stationary jaw 32 and the movable jaw 34 to the sides distant from the center in the Y direction.

Preferably, the width of the second electrode 44 is narrowed with respect to the probe distal end portion 32, with respect to the direction along the Y-axis orthogonal to the X-axis, to reduce the clearance C from the substantial center in the width direction of the stationary jaw 32 and the movable jaw 34 gradually toward the edge portions. Preferably, the width of the probe distal end portion is broadened with respect to the second electrode 44, with respect to the direction along the Y-axis orthogonal to the X-axis, to gradually decrease the clearance C from the substantial center in the width direction of the stationary jaw 32 and the movable jaw 34 toward the edge portions.

[Second Embodiment]

The following is explanation of the second embodiment with reference to FIG. 10 to FIG. 13B. The present embodiment is a modification of the first embodiment. Members that are the same, or having the same functions, as the members explained in the first embodiment are denoted by the same reference numerals, and detailed explanation is omitted.

This embodiment illustrates the example of including a treatment section 24 of a double-swinging type, unlike the treatment section 24 of a single-swinging type explained in the first embodiment. The first embodiment illustrates the case where treatment instrument 12 is capable of performing treatment of the living tissue with ultrasonic vibration, in addition to treatment of the living tissue with high-frequency energy. The present embodiment illustrates the treatment instrument 12 treating the living tissue only with a high-frequency output. For this reason, as illustrated in FIG. 10, the treatment unit 10 according to the present embodiment is not provided with ultrasonic transducer 26 illustrated in FIG. 1. In addition, the treatment unit 10 according to the present embodiment includes a foot switch 16 instead of the switch 50. The controller 14 and the foot switch 16 are detachable from each other.

As illustrated in FIG. 11A to FIG. 12B, the treatment section 24 is provided in the distal end portion of the treatment instrument main body 22. The treatment section 24 includes a first jaw (first clamp portion) 132, and a second jaw (second clamp portion) 134 movable between a position (closed position) adjacent to the first jaw 132 and a position (opened position) distant from the first jaw 132. The first and the second jaws 132 and 134 are supported by a pivot shaft 136 in the vicinity of the distal end portion of the treatment instrument main body 22. The first and the second jaws 132 and 134 move substantially symmetrically with respect to the pivot shaft 136. Because various publicly-known mechanisms such as a parallelogram link mechanism may properly be used as a mechanism for opening and closing the first and the second jaws 132 and 134, explanation of the mechanism is omitted herein. One pivot shaft 136 is illustrated in FIG. 11A and FIG. 11B in the present embodiment, but the jaws 132 and 134 may preferably be configured to rotate around respective pivot shafts (not illustrated).

The first jaw 132 is provided with the first electrode 42, and the second jaw 134 is provided with the second electrode 44. In the present embodiment, the first electrode 42 and the second electrode 44 are formed in a shape of flat plates that are substantially parallel in the closed position. When the first and the second jaws 132 and 134 are located in the closed position, the first and the second electrodes 42 and 44 are adjacent to each other, but separated from each other. The distance between the first and the second electrodes 42 and 44 in the closed position gradually increases toward the pivot shaft 136, and gradually decreases in a direction of going away from the pivot shaft 136. In the present embodiment, the first and the second electrodes 42 and 44 are separated from each other with an electric insulating stopper 182 provided on the first electrode 42. The stopper 182 regulates the clearance C of the electrode 44 of the second jaw 134 with respect to the electrode 42 of the first jaw 132, in the closed position. Accordingly, the stopper 182 regulates the range in which the first and the second jaws 132 and 134 are rotated around the pivot shaft 136.

The treatment section 24 illustrated in FIG. 11B holds no living tissue. In this state, in the state where the second jaw 134 is closed with respect to the first jaw 132, the gap (clearance) Ca between the second electrode 44 of the second jaw 134 and the first jaw 132 serving as the first electrode 42 illustrated in FIG. 12A is larger than the gap (clearance) Cb illustrated in FIG. 12B. In addition, as illustrated in FIG. 5B, the clearance C between the first electrode 42 of the first jaw 132 and the second electrode 44 of the second jaw 134 according to the present embodiment becomes larger toward the pivot shaft 136, and smaller in a direction of going away from the pivot shaft 136 along the X-axis. Specifically, the clearance C between the first electrode 42 of the first jaw 132 and the second electrode 44 of the second jaw 134 is formed to satisfy "Ca>Cb".

The following is explanation of functions of the treatment instrument 12 according to the present embodiment.

The treatment section 24 holds, for example, blood vessels having a longitudinal direction in a direction orthogonal to the X-axis. In this state, the treatment section 24 crushes the blood vessel illustrated in FIG. 13A illustrating a cross section (cross section in the first position) taken along line 12A-12A in FIG. 11B, and the blood vessel illustrated in FIG. 13B illustrating a cross section (cross section in the second position) taken along line 12B-12B in FIG. 11B, in the same manner. In the operation, the crush amounts of the blood vessels illustrated in FIG. 13A and FIG. 13B are substantially equal, and the clearances C in the positions illustrated in FIG. 13A and FIG. 13B are substantially equal in the positions.

Thereafter, when the operator presses the switch 16, the blood vessels are sealed with high-frequency output. When the blood vessels are sealed with high-frequency output, the blood vessels are held with a substantially uniform thickness as illustrated in FIG. 13A and FIG. 13B. For this reason, the blood vessels are substantially uniformly sealed from the side adjacent to the pivot shaft 136 to the side distant from the pivot shaft 136.

As explained above, the following can be said with the treatment instrument 12 according to the present embodiment.

The load pressure F between the first and the second jaws 132 and 134 reduces along the longitudinal direction (X-axis) in a direction of going away from the pivot shaft 136. This can be compensated, in particular, the crushing pressure of the living tissue in a position distant from the pivot shaft 136 is compensated, by adjusting the clearance C between the first and the second electrodes 42 and 44 of the first and the second jaws 132 and 134, that is, by gradually decreasing the clearance C herein. This structure substantially equalize the crushing amount to crush the living tissue in a position adjacent to the pivot shaft 136, and the crushing amount to crush the living tissue in a position distant from the pivot shaft 136 along the X-axis. Specifically, even when the load pressure F applied to the living tissue held between the first jaw 132 and the second jaw 134 differs, the treatment instrument 12 is capable of holding the living tissue by substantially uniform force over the whole length of the region of the held living tissue, by adjusting the clearance C. This structure enables exhibition of substantially fixed holding force to the living tissue, regardless of the position along the X-axis, in the first jaw 132 and the second jaw 134. Accordingly, when high-frequency energy is output to the living tissue, the energy can be uniformly input between the side adjacent to the pivot shaft 136 and the side distant from the pivot shaft 136. This structure substantially equalize the sealing capability of the living tissue such as a blood vessel, from the side adjacent to the pivot shaft 136 to the side distant from the pivot shaft 136 along the X-axis.

Also when the living tissue is coagulated using high-frequency output as well as blood vessels, this structure enables substantially uniform coagulation, in the same manner as blood vessels.

With respect to the example of using only high-frequency output, the present embodiment illustrates the case where the treatment section 24 is of a double-swinging type. As explained in the first embodiment, the treatment section 24 may be of a single-swinging type. In such a case, the insulating stopper 182 is provided on at least one of the first and the second electrodes 42 and 44. As another example, as illustrated in FIG. 7, the stoppers 82a may be formed between the first jaw 132 and the treatment instrument main body 22, and between the second jaw 134 and the treatment instrument main body 22.

[Third Embodiment]

The following is explanation of the third embodiment with reference to FIG. 14A to FIG. 17C. The present embodiment is a modification of the first and the second embodiments. Members that are the same, or having the same functions, as the members explained in the first and the second embodiments are denoted by the same reference numerals, and detailed explanation is omitted. The treatment instrument 12 is explained as a treatment instrument capable of outputting high-frequency output and ultrasonic output, in the same manner as explained in the first embodiment. The treatment instrument 12 may be configured to be capable of outputting only high-frequency output, as a matter of course.

As illustrated in FIG. 14A to FIG. 15C, the treatment section 24 includes the stationary jaw (first clamp portion) 32, a movable jaw 234, and a pivot member (second clamp portion) 236. The movable jaw 234 is supported by the treatment instrument main body 22, more specifically, the pivot shaft (first pivot shaft) 36 at the distal end of the sheath 22a, in the same manner as the movable jaw 34 explained in the first embodiment. The pivot member 236 is supported by the movable jaw 234 with a pivot shaft (second pivot shaft) 238 as a fulcrum. The pivot member 236 is located in a position more adjacent to the fix jaw 32 beyond the movable jaw 234. The pivot shafts 236 and 238 are preferably parallel with each other. The movable jaw 234 and the pivot member 236 move in linkage with each other, and are referred to as seesaw jaws or wiper jaws.

The movable jaw 234 is provided between the two pivot shafts 36 and 238, and capable of rotating the pivot member 236 with its pivot around the pivot shaft 36, and moving the pivot member 236 between the opened position and the closed position. Specifically, the pivot member 236 is movable between the position (opened position) illustrated in FIG. 14A in which the pivot member 236 is distant from the stationary jaw 32, and the position (closed position) illustrated in FIG. 14B in which the pivot member 236 is adjacent to the stationary jaw 32, with pivot of the movable jaw 234.

The pivot member 236 includes a pivot member main body 262, and the pressure pad (stopper) 64. The pivot member main body 262 is provided with the second electrode 44 in a position opposed to the first electrode 42 (stationary jaw 32). The second electrode 44 is formed in a state of holding the pressure pad 64 therebetween. The pivot member main body 262 may preferably be formed as one unitary piece with the second electrode 44. The pressure pad 64 is located in a position contacting the stationary jaw 32. By contrast, the second electrode 44 of the pivot member 236 can be disposed adjacent to the stationary jaw 32, that is, the first electrode 42, with the clearance C.

The stationary jaw 32 and the pivot member 262 include distal end portions (one end portions) 33a and 236a and proximal end portions (other end portions) 33b and 236b, respectively. The proximal end portions (the other end portions) 33b and 236b are located adjacent to the pivot shaft 36, and in the vicinity of the most proximal end in the position where the living tissue can be held. The clearance C is formed in a state of continuously extending from the distal end portions (one end portions) 33a and 236a of the stationary jaw 32 and the pivot member 236 to the proximal end portions (the other end portions) 33b and 236b. Specifically, the first and the second electrodes 42 and 44 are separated from each other from the distal end portions (one end portions) 33a and 236a of the stationary jaw 32 and the pivot member 236 to the proximal end portions (the other end portions) 33b and 236b, in the state where the pivot member 236 is in the closed position with respect to the stationary jaw 32.

When the movable handle 23b is relatively positioned adjacent to the stationary handle 23a of the treatment instrument main body 22, the movable jaw 234 is rotated around the pivot shaft 36 at the distal end of the treatment instrument main body 22, in linkage with the operation of the movable handle 23b, and the pivot member 236 supported by the movable jaw 234 is positioned adjacent to the stationary jaw 32. When the movable handle 23b is relatively positioned distant from the stationary handle 23a, the movable jaw 234 is rotated around the pivot shaft 36, in linkage with the operation of the movable handle 23b, and the pivot member 236 supported by the movable jaw 234 is positioned distant from the stationary jaw 32, together with the movable jaw 234.

The stationary jaw 32, the movable jaw 234, and the pivot member 236 have longitudinal sizes larger than their sizes in the width direction. The maximum widths of the stationary jaw 32, the movable jaw 234, and the pivot member 236 are determined, for example, based on relation with the internal diameter of the trocar.

Figure 14A:
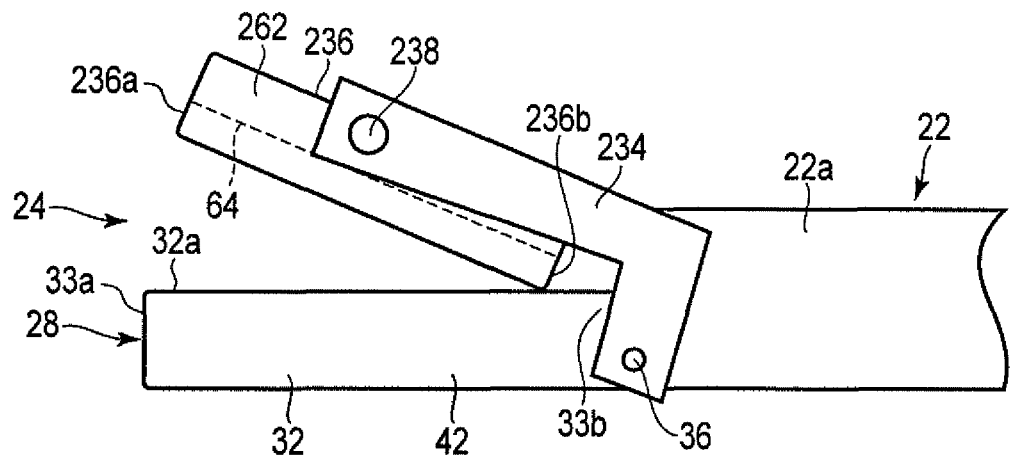
FIG. 14A is a schematic diagram illustrating a state of an opened position in which a movable jaw of a treatment instrument of a medical apparatus unit according to a third embodiment is opened, to open a pivotal member (clamp portion) linked with the movable jaw with respect to the stationary jaw.
Figure 14B:
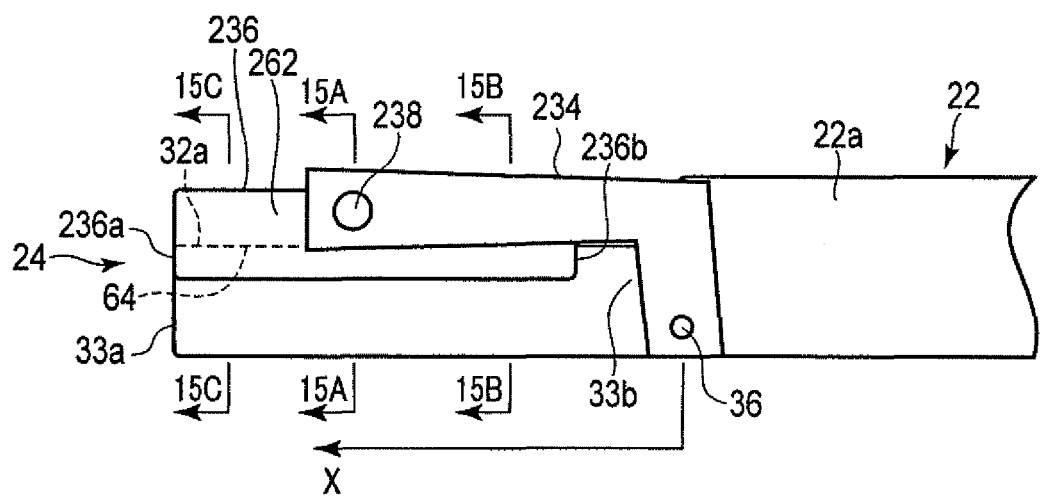
FIG. 14B is a schematic diagram illustrating a state of an closed position in which the movable jaw of the treatment instrument of the medical apparatus unit according to the third embodiment is closed, to close the pivotal member linked with the movable jaw with respect to the stationary jaw.
Figure 16A:
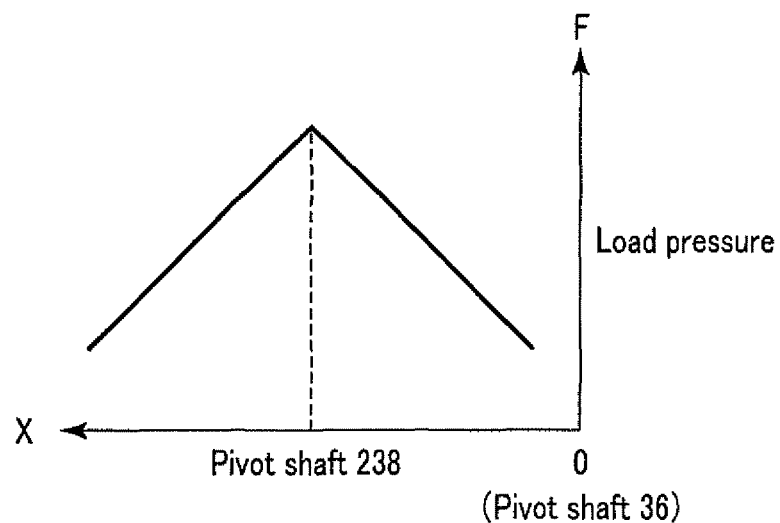
FIG. 16A is a schematic diagram illustrating load pressure with respect to the position of the pivotal member at the time when the load pressure is to be applied to the living tissue, in a state where the pivotal member (clamp portion) of the treatment instrument according to the third embodiment is rotated to the closed position.

As illustrated in FIG. 14B, an X-axis is set with the pivot shaft 36 serving as the origin O. In particular, the X-axis is set to extend from the pivot shaft 36 of the movable jaw 234 in an extending direction opposite to the treatment instrument main body 22. In a state of the closed position in which the pivot member 236 supported by the movable jaw 234 is adjacent to the stationary jaw 32, the pressure (load pressure) F applicable to the living tissue by the pivot member 236 of the movable jaw 34 along its longitudinal direction (X-axis direction) schematically distributes in a state illustrated in FIG. 16A. In the state where the pivot member 236 supported by the movable jaw 234 is closed with respect to the stationary jaw 32, as illustrated in FIG. 16A, the pivot member 236 supported by the movable jaw 234 is capable of applying larger pressure to the living tissue held between it and the stationary jaw 32, in a position more adjacent to the pivot shaft 238. For this reason, the pivot member 236 supported by the movable jaw 234 decreases the force applied to the living tissue held between it and the stationary jaw 32, as the position becomes distant from the pivot shaft 238.

Figure 15A:
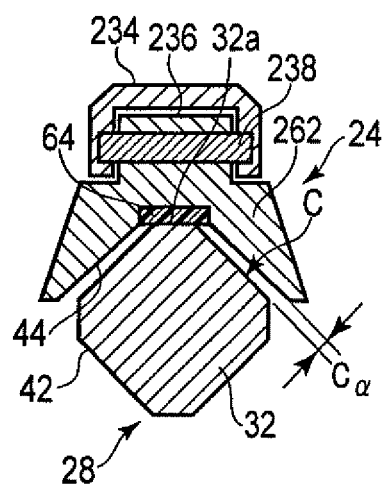
FIG. 15A is a schematic lateral cross-sectional view in a position along line 15A-15A in FIG. 14B.
Figure 15B:
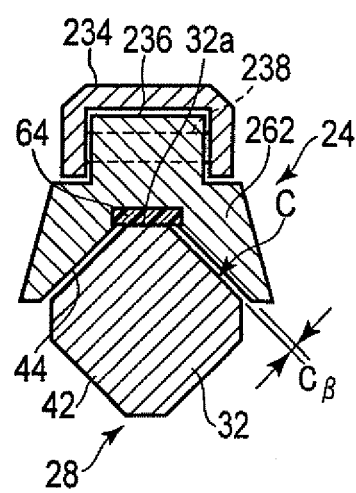
FIG. 15B is a schematic lateral cross-sectional view in a position along line 15B-15B in FIG. 14B.
Figure 15C:
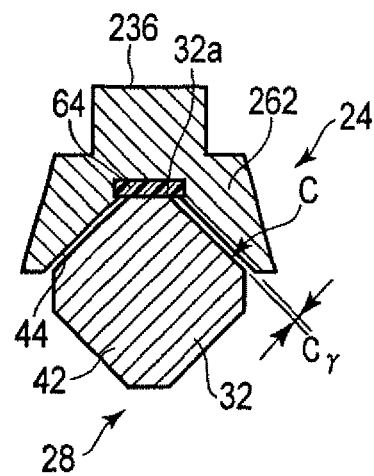
FIG. 15C is a schematic lateral cross-sectional view in a position along line 15C-15C in FIG. 14B.
Figure 16B:
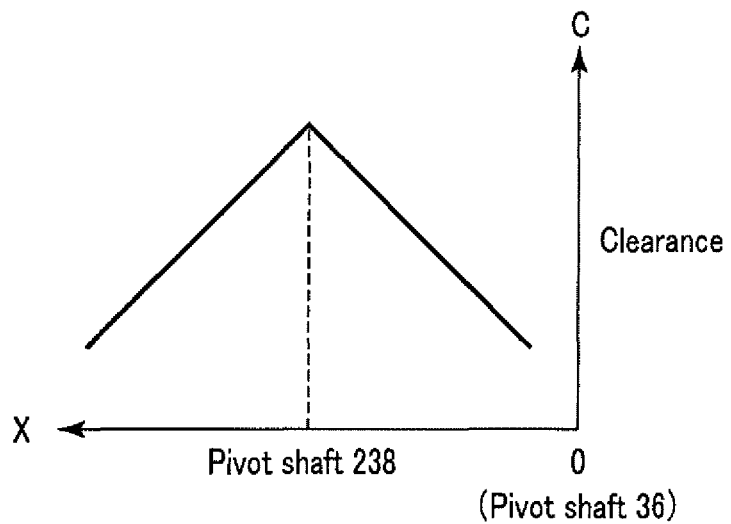
FIG. 16B is a schematic diagram illustrating a size of clearance from the stationary jaw with respect to the position of the pivotal member, in the state where the pivotal member of the treatment instrument according to the third embodiment is rotated to the closed position.

The treatment section 24 illustrated in FIG. 14B holds no living tissue. In this state, in the state where the movable jaw 34 is closed with respect to the stationary jaw 32, the gap (clearance) $C\alpha$ between the second electrode 44 of the pivot member 236 supported by the movable jaw 34 and the stationary jaw 32 serving as the first electrode 42 illustrated in FIG. 15A is larger than the gap (clearance) $C\beta$ illustrated in FIG. 15B, and the gap (clearance) $C\gamma$ illustrated in FIG. 15C. In addition, as illustrated in FIG. 16B, the clearance C between the second electrode 44 of the pivot member 236 according to the present embodiment and the stationary jaw 32 serving as the first electrode 42 is larger in a position closer to the pivot shaft 238 of the pivot member 236, and smaller in a position more distant from the pivot shaft 238 along the X-axis. Specifically, the clearance C between the second electrode 44 of the pivot member 236 and the stationary jaw 32 serving as the first electrode 42 is formed to satisfy "$C\alpha > C\beta$" and "$C\alpha > C\gamma$".

As illustrated in FIG. 16B, the clearance C is set to be linearly (in a straight line manner) smaller from the position adjacent to the pivot shaft 238 toward the position distant from the pivot shaft 238 along the X-axis. For example, the clearance $C\alpha$ is approximately 0.2 mm in the position illustrated in FIG. 15A, the clearance $C\beta$ is approximately 0.1 mm in the position illustrated in FIG. 15B, and the clearance $C\gamma$ is approximately 0.1 mm in the position illustrated in FIG. 15C. The clearance C larger than 0 (C>0) is maintained along the X-axis between the second electrode 44 of the movable jaw 234 and the stationary jaw 32 serving as the first electrode 42.

The following is explanation of functions of the treatment instrument 12 according to the present embodiment.

Figure 17A:
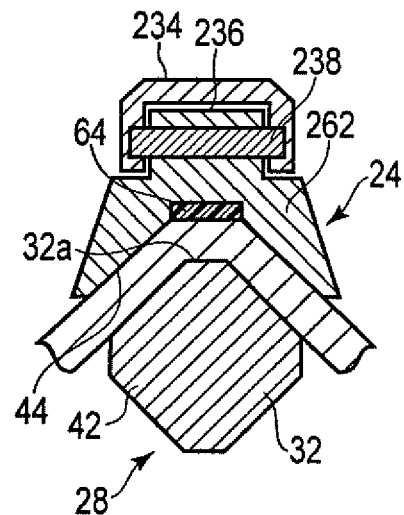
FIG. 17A is a schematic lateral cross-sectional view illustrating a state where the living tissue is held in the position along line 15A-15A in FIG. 14B.
Figure 17B:
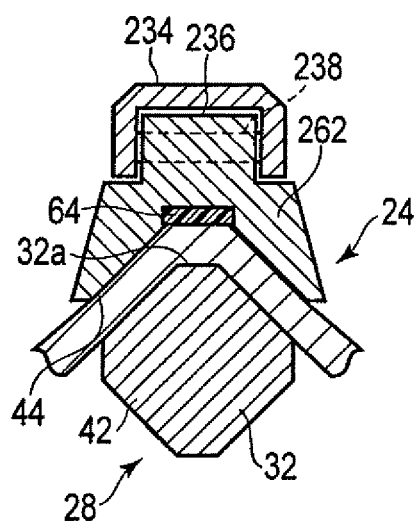
FIG. 17B is a schematic lateral cross-sectional view illustrating a state where the living tissue is held in the position along line 15B-15B in FIG. 14B.
Figure 17C:
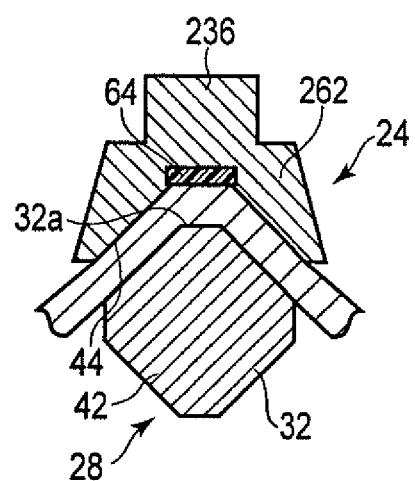
FIG. 17C is a schematic lateral cross-sectional view illustrating a state where the living tissue is held in the position along line 15C-15C in FIG. 14B.

For example, the treatment section 24 holds, for example, blood vessels having a longitudinal direction in a direction orthogonal to the X-axis. In this state, the treatment section 24 crushes the blood vessel illustrated in FIG. 17A illustrating a cross section (cross section in the first position) taken along line 15A-15A in FIG. 14B, the blood vessel illustrated in FIG. 17B illustrating a cross section (cross section in the second position) taken along line 15B-15B in FIG. 14B, and the blood vessel illustrated in FIG. 17C illustrating a cross section (cross section in the third position) taken along line 15C-15C in FIG. 14B, in the same manner. In the operation, the crush amounts of the blood vessels illustrated in FIG.

17A to FIG. 17C are substantially equal, and the clearance C is substantially equal in the positions illustrated in FIG. 17A to FIG. 17C.

Thereafter, when the operator presses the first switch 52, the blood vessels are sealed with high-frequency output. When the blood vessels are sealed with high-frequency output, the blood vessels are held with a substantially uniform thickness as illustrated in FIG. 17A to FIG. 17C. For this reason, the blood vessels are substantially uniformly sealed in any position from the distal end portion 236a to the proximal end portion 236b of the pivot member 236.

By contrast, for example, when the operator presses the second switch 54, the blood vessels are cut by ultrasonic output, while being sealed by high-frequency output. When the high-frequency output and the ultrasonic output are simultaneously output to cut the blood vessels while the blood vessels are sealed, the blood vessels are substantially uniformly sealed as described above. For this reason, the blood vessels are cut in a state in which miss of seal hardly occurs.

As explained above, the following can be said with the treatment instrument 12 according to the present embodiment.

The load pressure F of the pivot member 236 reduces along the longitudinal direction (X-axis) in a direction of going away from the pivot shaft 238. The crushing pressure of the living tissue is compensated, by adjusting the clearance C between the first electrode 42 of the stationary jaw 32 and the second electrode 44 of the pivot member 236, that is, by gradually decreasing the clearance C herein. This structure substantially equalize the crushing amount to crush the living tissue in a position adjacent to the pivot shaft 238, and the crushing amount to crush the living tissue in a position distant from the pivot shaft 238 along the X-axis. Specifically, even when the load pressure F applied to the living tissue held between the stationary jaw 132 and the pivot member 236 differs, the treatment instrument 12 is capable of holding the living tissue by substantially uniform force over the whole length of the region of the held living tissue, by adjusting the clearance C. This structure enables exhibition of substantially fixed holding force to the living tissue, regardless of the position along the X-axis, in the first jaw 32 and the pivot member 236. Accordingly, when high-frequency energy is output to the living tissue, the energy can be uniformly input between the side adjacent to the pivot shaft 238 and the side distant from the pivot shaft 238. This structure substantially equalize the sealing capability of the living tissue such as a blood vessel, from the side adjacent to the pivot shaft 238 to the side distant from the pivot shaft 238 along the X-axis.

When the living tissue such as a blood vessel is cut, the sealing capability is substantially made uniform. This structure more securely prevents occurrence of miss of seal for a blood vessel in cutting the blood vessel, and prevents discharge of the blood.

Also when the living tissue is coagulated using high-frequency output as well as blood vessels, this structure enables substantially uniform coagulation, in the same manner as blood vessels. In addition, when the living tissue such as a blood vessel is cut, the sealing capability is substantially made uniform. This structure more securely prevents occurrence of miss of coagulation for a living tissue in cutting the living tissue.

Figure 16C:
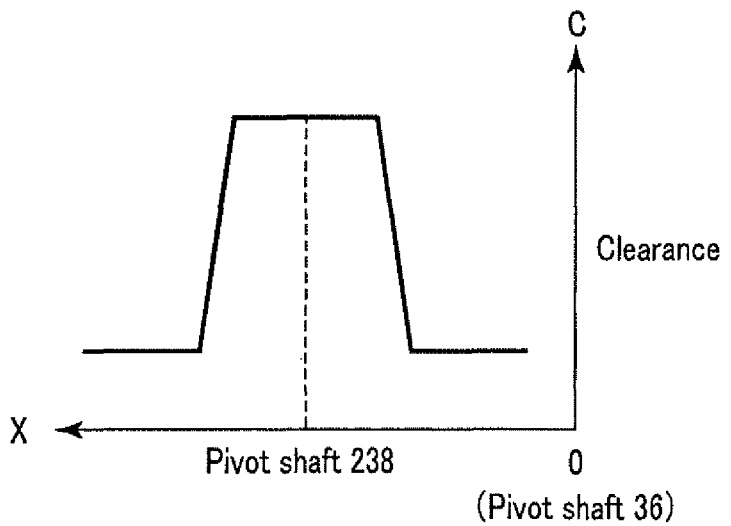
FIG. 16C is a schematic diagram illustrating a size of clearance from the stationary jaw with respect to the position of the pivotal member, in the state where the pivotal member of the treatment instrument according to a modification of the third embodiment is rotated to the closed position.

The present embodiment illustrates the example of forming the clearance C as illustrated in FIG. 16B. As another example, as illustrated in FIG. 16C, the clearance C may be preferably reduced in a stepped manner, as the position becomes distant from the pivot shaft 238 along the X-axis. In such a case, the holding force to the living tissue can be adjusted in accordance with the position separated from the pivot shaft 238, that is, the position with respect to the pivot shaft 238. This structure enables the treatment section 24 to change the holding force to the living tissue in accordance with the position along the longitudinal direction. The clearance C may be formed by adjusting the width between the probe distal end portion 32 and the second electrode 44 along the Y-axis direction orthogonal to the X-axis, or may be formed by adjusting the width of the probe distal end portion 32 along the Y-axis direction orthogonal to the X-axis with respect to the second electrode 44. Preferably, the width of the second electrode 44 is narrowed with respect to the probe distal end portion 32 with respect to the direction along the Y-axis direction orthogonal to the X-axis, to reduce the clearance C gradually from the center side toward the edge portion sides. As another example, preferably, the width of the probe distal end portion 32 is broadened with respect to the second electrode 44 with respect to the direction along the Y-axis direction orthogonal to the X-axis, to reduce the clearance C gradually from the center side toward the edge portion sides.

The reducing mechanism of the clearance C as the position becomes more distant from the pivot shaft 238 is not limited to the state illustrated in FIG. 16B or the state illustrated in FIG. 16C.

As a matter of course, the double-swinging type first jaw 132 illustrated in FIG. 11A and FIG. 11B explained in the second embodiment can be provided with the pivot shaft 238 to rotatably support the pivot member 236, and the second jaw 134 can be provided with the pivot shaft 238 to rotatably support the pivot member 236. In this case, the pivot members 236 are opposed to each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical apparatus comprising:
   a first clamp portion including a distal end portion and a proximal end portion, the first clamp portion extending along a longitudinal direction, and configured to function as a first electrode;
   a first pivot shaft adjacent to the proximal end portion of the first clamp portion;
   a movable jaw rotatable around the first pivot shaft between an opened condition in which the movable jaw is distant from the first clamp portion and a closed condition in which the movable jaw is adjacent to the first clamp portion;
   a second pivot shaft parallel with the first pivot shaft;
   a pivot member movably attached to the movable jaw with the second pivot shaft serving as fulcrum; and
   a second electrode opposed to the first electrode and provided in the pivot member, wherein when the movable jaw is adjacent to the first clamp portion, the first electrode and the second electrode form a clearance therebetween that decreases as a distance from the second pivot shaft increases such that the clearance is at a maximum at the second pivot shaft and at a minimum at the proximal-most and distal-most ends of the second electrode.

2. The medical apparatus according to claim 1, wherein the clearance decreases in a stepped manner.

3. The medical apparatus according to claim 1, wherein the clearance gradually decreases from a center in a width direction of the first clamp portion and the movable jaw, the width direction being based on two ends of the first clamp portion and two ends of the movable jaw and different from the longitudinal direction of the first clamp portion and the movable jaw.

4. The medical apparatus according to claim 3, wherein the movable jaw comprises a pressure pad, and the clearance is larger in a position closer to the center in the width direction and smaller in a position more distant from the center in the width direction, except for a position in which the first clamp portion contacts the pressure pad of the movable jaw.

5. The medical apparatus according to claim 1, wherein the medical apparatus is configured to control the first electrode and the second electrode to have different potentials so that a high-frequency output passes through a living tissue between the first electrode and the second electrode.

6. The medical apparatus according to claim 5, further comprising: a stopper configured for regulating a range in which the movable jaw is rotated around the first pivot shaft, and regulating the clearance of the second electrode with respect to the first electrode of the first clamp portion in the closed condition.

7. The medical apparatus according to claim 6, wherein the stopper has electric insulating property.

8. The medical apparatus according to claim 6, wherein the stopper is configured to separate the first clamp portion from the second electrode provided in the movable jaw in the closed condition.

9. The medical apparatus according to claim 5, wherein the first clamp portion is formed as a vibration transmission member having conductivity and capable of transmitting ultrasonic vibration.

10. The medical apparatus according to claim 1, wherein the clearance decreases linearly from a position adjacent to the second pivot shaft toward a position distant from the second pivot shaft.

* * * * *